United States Patent
Irving et al.

(10) Patent No.: US 11,327,048 B2
(45) Date of Patent: May 10, 2022

(54) METHODS AND APPARATUS FOR PERFORMING SAMPLE MEASUREMENTS USING VISIBLE LIGHT ON SAMPLES MANIPULATED WITH ACOUSTIC WAVES

(71) Applicant: Siemens Healthcare Diagnostics Inc., Tarrytown, NY (US)

(72) Inventors: Ryan Irving, Norwood, MA (US); Peter Paulicka, Röttenbach (DE)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 17/593,653

(22) PCT Filed: Mar. 20, 2020

(86) PCT No.: PCT/US2020/023823
§ 371 (c)(1),
(2) Date: Sep. 22, 2021

(87) PCT Pub. No.: WO2020/197993
PCT Pub. Date: Oct. 1, 2020

(65) Prior Publication Data
US 2022/0091068 A1 Mar. 24, 2022

Related U.S. Application Data

(60) Provisional application No. 62/823,824, filed on Mar. 26, 2019.

(51) Int. Cl.
*G01N 29/02* (2006.01)
*B01L 3/00* (2006.01)
(Continued)

(52) U.S. Cl.
CPC ........ *G01N 29/02* (2013.01); *B01L 3/502715* (2013.01); *B01L 3/523* (2013.01); *B01L 2200/0689* (2013.01); *B01L 2300/0816* (2013.01); *B01L 2300/168* (2013.01); *B01L 2400/06* (2013.01); *B01L 2400/082* (2013.01);
(Continued)

(58) Field of Classification Search
CPC ................ G01N 29/02; G01N 33/543; G01N 33/54373; B01L 3/502715; B01L 2200/0689; B01L 2300/0816; A61B 5/00; A61B 5/145; A61B 5/0031; A61B 5/0071
See application file for complete search history.

(56) References Cited

U.S. PATENT DOCUMENTS 6,330,464 B1  12/2001  Covin, Jr. et al.
6,845,327 B2  1/2005  Lauks
(Continued)

OTHER PUBLICATIONS

International Search Report and Written Opinion of International Application No. PCT/US2020/023823 dated May 22, 2020.
(Continued)

*Primary Examiner* — Brian J. Sines (57) ABSTRACT

An acoustic analyzer system is provided that includes an acoustic analyzer having a reusable glass flow cell positioned within the acoustic analyzer. A disposable card body may be inserted into the acoustic analyzer and deliver sample fluid to the glass flow cell so that acoustic-wave assisted measurements may be performed on the sample fluid. The disposable card body may also deliver wash fluid to the glass flow cell, and receive waste sample fluid and waste wash fluid from the glass flow cell to prepare the glass flow cell for subsequent sample fluids. Numerous other embodiments are provided.

20 Claims, 7 Drawing Sheets

(52) U.S. Cl.
CPC . *G01N 2291/021* (2013.01); *G01N 2291/101* (2013.01)

(56) References Cited

U.S. PATENT DOCUMENTS

| | | |
|---|---|---|
| 6,896,778 B2 | 5/2005 | Lauks |
| 7,094,330 B2 | 8/2006 | Lauks et al. |
| 7,523,649 B2 | 4/2009 | Corey et al. |
| 7,722,817 B2 | 5/2010 | Lauks et al. |
| 7,767,068 B2 | 8/2010 | Lauks et al. |
| 7,857,761 B2 | 12/2010 | Lec et al. |
| 2010/0252428 A1 | 10/2010 | Lauks et al. |
| 2012/0271123 A1 | 10/2012 | Castle et al. |
| 2019/0176149 A1 | 6/2019 | Shachar et al. |

OTHER PUBLICATIONS

Axel Tojo, "Free Flow Acoustophoresis" Technology Transfer from Silicon to Glass, Nov. 2012, Lund University Master's Thesis, pp. 1-61.

Klara Petersson, "Clinical Applications of Acoustophoresis in Blood Based Diagnostics", Feb. 2018, Lund University Doctoral Dissertation, pp. 1-110.

METHODS AND APPARATUS FOR PERFORMING SAMPLE MEASUREMENTS USING VISIBLE LIGHT ON SAMPLES MANIPULATED WITH ACOUSTIC WAVES

This application claims the benefit of provisional patent application Ser. No. 62/823,824, filed on Mar. 26, 2019, the entire contents of which are hereby incorporated herein by reference.

FIELD

The present application relates to diagnostic testing, and more particularly to methods and apparatus for performing sample measurements using visible light on samples manipulated with acoustic waves.

BACKGROUND

Acoustic waves may be employed to separate components of blood. For example, red blood cells may be separated from other components of a blood sample using standing acoustic waves (e.g., acoustophoresis). Such separation techniques may rely on differences in density and/or radius of the blood components, for example.

Rapidly and cost effectively performing blood component separation using acoustic waves is difficult. Accordingly, improved systems, methods and apparatus for employing acoustic wave separation techniques on blood or other samples are desired.

SUMMARY

In some embodiments provided herein, a diagnostic card assembly includes a card body configured for insertion into an acoustic analyzer. The card body includes (1) a sample inlet port positioned to receive sample fluid; (2) a waste inlet port; (3) an outlet port; (4) a first fluid conduit extending between the sample inlet port and the outlet port; (5) a wash fluid chamber configured to hold a wash fluid; (6) a second fluid conduit extending between the wash fluid chamber and the outlet port; (7) a valve connecting the wash fluid chamber to the second fluid conduit and configured to control flow of wash fluid from the wash fluid chamber when the card body is inserted into the acoustic analyzer; (8) a waste fluid region configured to store waste sample fluid and waste wash fluid; and (9) a third fluid conduit extending between the waste input port and the waste fluid region. The card body is configured to be inserted into an acoustic analyzer and to sealingly couple to a glass flow cell within the acoustic analyzer, deliver sample fluid and wash fluid through the outlet port of the card body to a channel of the glass flow cell, and receive waste sample fluid and waste wash fluid from the glass flow cell.

In some embodiments provided herein, an acoustic analyzer includes (1) an opening configured to receive a disposable card body having a sample inlet port, a waste inlet port, an outlet port, a wash fluid chamber and a waste fluid region; (2) a mounting location positioned within the opening and configured to hold a replaceable, multi-use glass flow cell within the acoustic analyzer such that the glass flow cell sealingly couples to the disposable card body when the disposable card body is inserted into the acoustic analyzer; and (3) a transducer configured to generate standing waves in a channel of any glass flow cell positioned within the mounting location so as to spatially separate one or more components of a sample fluid within the channel.

In some embodiments provided herein, an acoustic analyzer system includes (1) an acoustic analyzer configured to receive a disposable card body; and (2) a replaceable, multi-use glass flow cell positioned within the acoustic analyzer and configured to sealingly couple to the disposable card body when the disposable card body is inserted into the acoustic analyzer, the glass flow cell including an inlet, an outlet and a channel extending between the inlet and the outlet. The inlet of the glass flow cell is configured to receive sample fluid and wash fluid from an outlet port of the disposable card body, direct flow of sample fluid and wash fluid through the channel and to the outlet of the glass flow cell. The outlet of the glass flow cell is configured to provide sample fluid and wash fluid to a waste inlet port of the disposable card body.

In some embodiments provided herein, a method of using an acoustic analyzer includes (1) receiving a card body within the acoustic analyzer, the card body including (a) a sample inlet port positioned to receive sample fluid; (b) a waste inlet port; (c) an outlet port; (d) a first fluid conduit extending between the sample inlet port and the outlet port; (e) a wash fluid chamber configured to hold a wash fluid; (f) a second fluid conduit extending between the wash fluid chamber and the outlet port; (g) a valve connecting the wash fluid chamber to the second fluid conduit and configured to control flow of wash fluid from the wash fluid chamber when the card body is inserted into the acoustic analyzer; (h) a waste fluid region configured to store waste sample fluid and waste wash fluid; and (i) a third fluid conduit extending between the waste inlet port and the waste fluid region; and (2) sealing the card body against a glass flow cell positioned with the acoustic analyzer, the glass flow cell including an inlet, an outlet and a channel extending between the inlet and the outlet. The inlet of the glass flow cell is configured to receive sample fluid and wash fluid from the outlet port of the card body, direct flow of sample fluid and wash fluid through the channel and to the outlet of the glass flow cell. The outlet of the glass flow cell is configured to provide sample fluid and wash fluid to the waste inlet port of the card body. The method further includes (3) receiving a sample fluid at the sample inlet port of the card body; (4) directing the sample fluid through the first fluid conduit, through the outlet port of the card body and through the inlet of the glass flow cell into the channel of the glass flow cell; (5) analyzing the sample fluid using the acoustic analyzer; and (6) directing the sample fluid from the channel of the glass flow cell through the outlet of the glass flow cell, through the waste inlet port of the card body, and through the third fluid conduit to the waste fluid region of the card body.

Other features and aspects of the present invention will become more fully apparent from the following detailed description, the appended claims, and the accompanying drawings.

DETAILED DESCRIPTION

In some embodiments, an acoustic analyzer may be provided which includes a reusable glass flow cell that interfaces with a disposable card body. The disposable card body may be, for example, a single use card body. The disposable card body may be inserted into the acoustic analyzer and deliver sample fluid to the glass flow cell so that acoustic-wave assisted measurements may be performed on the sample fluid. The disposable card body may also deliver wash fluid to the glass flow cell, and receive waste sample fluid and waste wash fluid from the glass flow cell to prepare the glass flow cell for subsequent sample fluids. Such a system may allow for inexpensive and rapid testing of sample fluid, including a blood sample, using acoustophoresis as described further below.

In some embodiments, the disposable card body may include a sample fluid delivery conduit, a wash fluid region for storing wash fluid, and a waste fluid region. The disposable card body may be inserted into the acoustic analyzer, and the reusable glass flow cell may interface with the disposable card body within the analyzer. Thereafter, a syringe or similar delivery mechanism may provide sample fluid into the channel of the glass flow cell using the sample fluid delivery conduit of the disposable card body. The acoustic analyzer may then perform one or more acoustic-wave assisted measurements on the sample fluid. Following these measurements, the wash fluid region of the disposable card body may deliver wash fluid to the channel of the glass flow cell to prepare the glass flow cell for another sample. Waste sample fluid and waste wash fluid may be stored on the disposable card body within the waste fluid region. The disposable card body may then be discarded, leaving the acoustic analyzer ready to receive a new disposable card body, and other sample fluid.

The disposable card body may be formed from an inexpensive plastic material which includes the fluid delivery conduits, valve, wash fluid region, wash fluid, and waste fluid region used for delivery of a sample to the analyzer, cleaning of the glass flow cell and storage of any waste fluids. Unlike the glass of a glass flow cell, plastic may lack the stiffness and optical clarity needed for acoustophoresis. By interfacing the disposable card body with the glass flow cell within the analyzer, components of a sample fluid (e.g., blood) may be manipulated within the glass flow cell using acoustic techniques such as acoustophoresis, and the disposable card body may be used for sample fluid and wash fluid delivery, as well as for waste fluid disposal. In some embodiments, the glass flow cell may be re-used between 100 to 1000 times before replacement.

In accordance with embodiments described herein, an acoustic standing wave pattern may be generated within the channel of the glass flow cell using one or more acoustic transducers. In some embodiments, the acoustic standing wave pattern may be employed to separate red blood cells from other components of a blood sample (e.g., plasma, leukocytes, platelets, etc.). One or more wavelengths of light (e.g., red, orange, yellow, green, blue, indigo or violet) may then be used to probe the blood components to detect lipid level, bilirubin level, hemolysis level, free hemoglobin, or the like.

These and other embodiments of the present disclosure are described below with reference to FIGS. 1A-6.

Figure 1A:
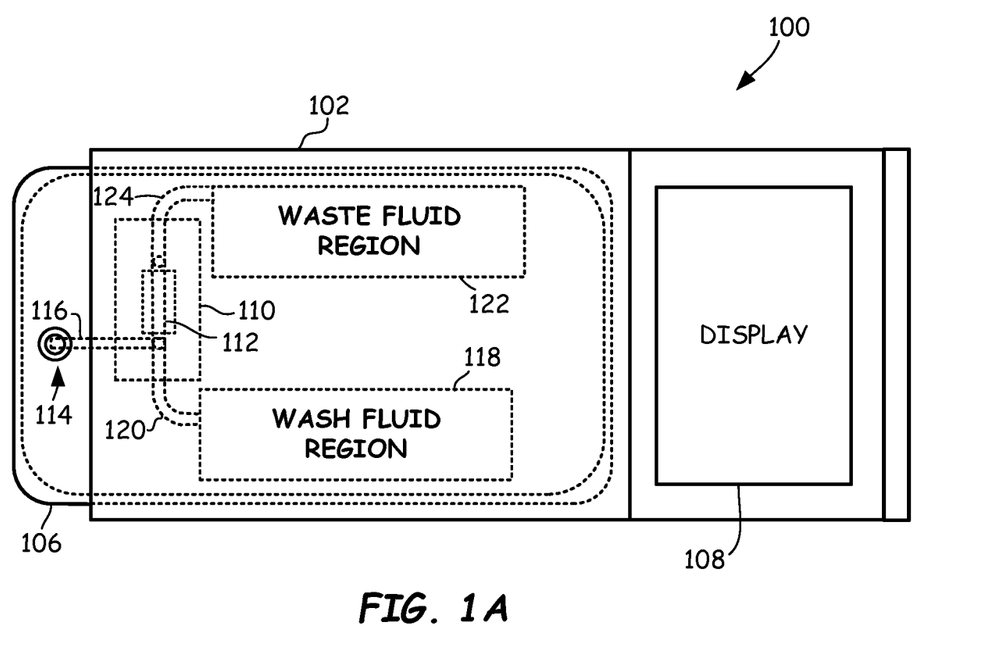
FIGS. 1A and 1B illustrate a top plan view and a side plan view, respectively, of an example acoustic analyzer system in accordance with embodiments provided herein.
Figure 1B:
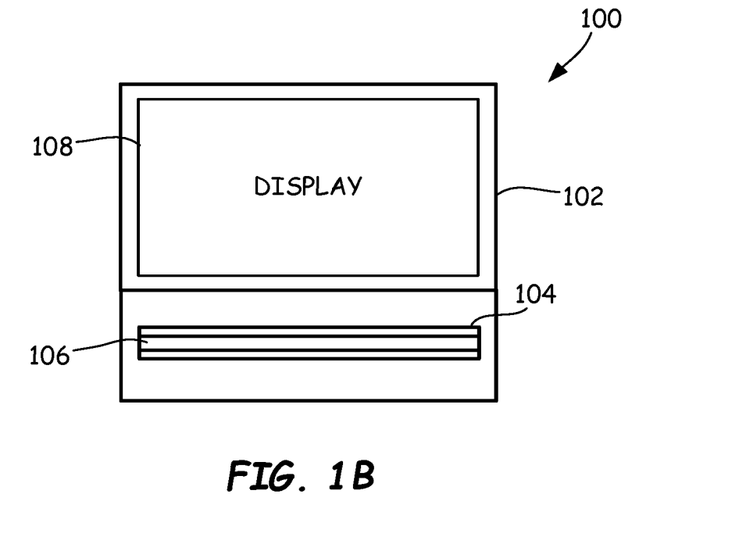

With reference to FIGS. 1A and 1B, a top plan view and a side plan view, respectively, of an example acoustic analyzer system 100 is shown in accordance with embodiments provided herein. Acoustic analyzer system 100 includes an acoustic analyzer 102 that has an opening 104 for receiving a disposable card body 106. Disposable card body 106 may be inserted in or removed from opening 104 of acoustic analyzer 102 as described further below. In some embodiments, acoustic analyzer 102 may include a display 108 having a user interface (not separately shown) that allows an operator to control operation of the acoustic analyzer 102, observe measurement results from testing performed by the acoustic analyzer 102, communicate measurement results to an external device such as a printer or a patient management system, etc. The portion of the acoustic analyzer 102 which houses the display 108 may be tiltable and/or detachable, in some embodiments.

As shown in FIG. 1A, acoustic analyzer 102 includes a glass flow cell 110 having a channel 112 in which a sample fluid is contained during testing with the acoustic analyzer 102. Disposable card body 106 includes a sample inlet port 114 coupled to a first fluid conduit 116, a wash fluid region 118 coupled to a second fluid conduit 120, and a waste fluid region 122 coupled to a third fluid conduit 124. When disposable card body 106 is inserted into acoustic analyzer 102, first fluid conduit 116 couples sample inlet port 114 to glass flow cell 110, second fluid conduit 120 couples wash fluid chamber 118 to glass flow cell 110, and third fluid conduit 124 couples waste fluid region 122 to glass flow cell 110.

Operation of acoustic analyzer 102 is described in detail with reference to FIGS. 5A-6. In general, disposable card body 106 may be inserted into opening 104 of acoustic analyzer 102 so as to interface with glass flow cell 110. Sample inlet port 114 is positioned to receive sample fluid, such as a blood sample contained within a syringe, and to employ first fluid conduit 116 (also referred to as a sample fluid delivery conduit) of disposable card body 106 to deliver the sample fluid to channel 112 of glass flow cell 110. Acoustic analyzer 102 may then perform one or more measurements on the sample fluid (e.g., acoustophoresis-assisted hemolysis analysis) within channel 112 of glass flow cell 110.

Following measurements within glass flow cell 110, wash fluid may be provided to channel 112 from wash fluid region 118 through second fluid conduit 120. For example, a bleach or other wash fluid solution may be delivered to channel 112 of glass flow cell 110 to remove sample fluid from channel 112 and prepare glass flow cell 110 for another sample. Waste sample fluid and waste wash fluid may travel through third fluid conduit 124 for storage in waste fluid region 122 of disposable card body 106. Disposable card body 106 may then be removed from acoustic analyzer 102 and discarded, leaving glass flow cell 110 ready to receive another sample delivered using a different disposable card body (not shown).

Figure 2A:
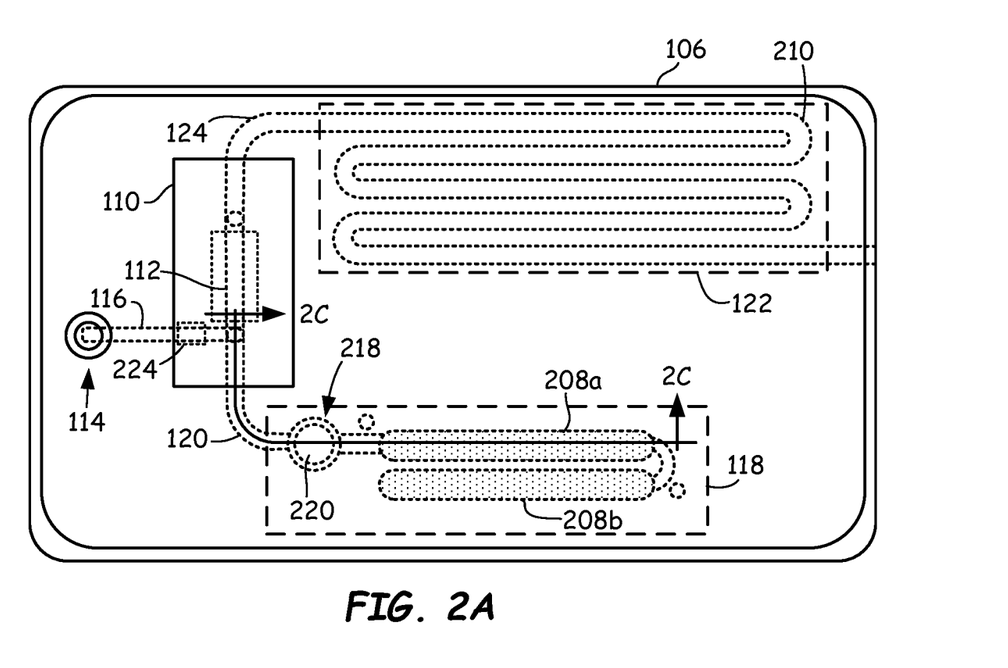
FIGS. 2A and 2B illustrate a top plan view and a side plan view, respectively, of an example embodiment of a disposable card body shown interfaced with a glass flow cell in accordance with embodiments provided herein.
Figure 2B:
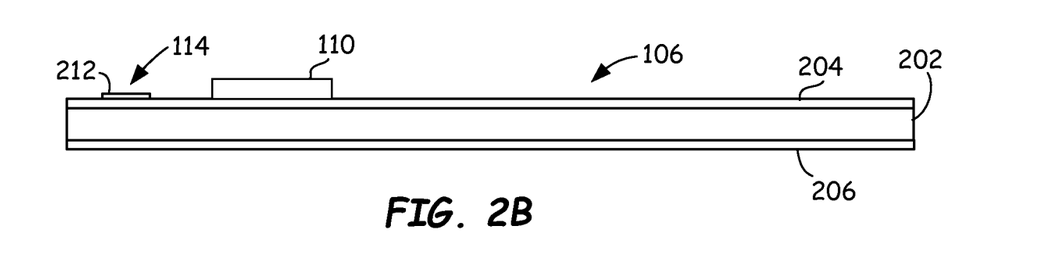

FIGS. 2A and 2B illustrate a top plan view and a side plan view, respectively, of an example embodiment of disposable card body 106 shown interfaced with glass flow cell 110. As shown in FIG. 2B, in some embodiments, disposable card body 106 may include an inner region 202 having a top layer 204 and a bottom layer 206 formed thereon. Inner region 202 may be formed, for example, from a plastic material such as polycarbonate or a similar material. Top layer 204 and bottom layer 206 may be formed, for example, from a laminate material such as an adhesive coated polymer sheet or a similar material. In some embodiments, top layer 204 and/or bottom layer 206 may include labelling for card body 106, such as insertion directions for card body 106.

Wash fluid region 118 may be formed within disposable card body 106 by one or more interconnected wash fluid chambers, for example. In the embodiment of FIG. 2A, two wash fluid chambers 208a, 208b are shown. Fewer or more wash fluid chambers may be used. Wash fluid chambers 208a, 208b may be formed, for example, as trenches, grooves, or similar structures molded within inner region 202 of disposable card body 106.

In some embodiments, waste fluid region 122 may be formed as a serpentine fluid conduit 210 having a length sufficient to hold waste sample fluid and waste wash fluid from channel 112 of glass flow cell 110. Serpentine fluid conduit 210 may be formed as a serpentine trench, groove, or similar structure molded within inner region 202 of disposable card body 106, for example.

First fluid conduit 116, second fluid conduit 120 and third fluid conduit 124 also may be formed as trenches, grooves or similar structures molded within inner region 202 of disposable card body 106. Sample inlet port 114 may include a hole that extends through top layer 204 and inner region 202 to first fluid conduit 116. A sealing member 212, such as an adhesive element, may be included at sample inlet port 114 for engaging a syringe or other sample fluid containing device (not shown) that delivers sample fluid to sample inlet port 114. Other configurations for wash fluid region 118, waste fluid region 122, and/or conduits 116, 120 and 124 may be employed.

Figure 2C:
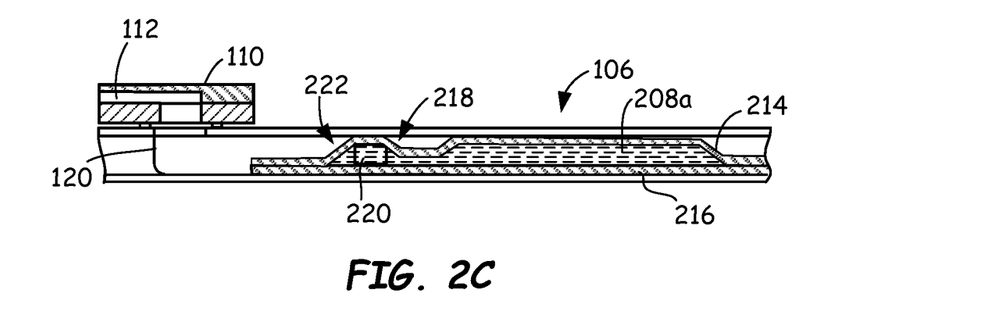
FIG. 2C illustrates an example cross section view of the disposable card body of FIG. 2A taken along fluidic path 2C-2C in FIG. 2A in accordance with embodiments provided herein.

FIG. 2C illustrates an example cross section view of disposable card body 106 taken along fluidic path 2C-2C in FIG. 2A. With reference to FIG. 2C, wash fluid chamber 208a may be formed between a top membrane 214 and a bottom membrane 216. For example, top membrane 214 and/or bottom membrane 216 may be formed from a metal foil film or similar material.

In some embodiments, a valve 218 may be formed within disposable card body 106 to control flow of wash fluid from wash fluid region 118 into glass flow cell 110. For example, valve 218 may include a movable plug 220 that may be elevated (e.g., by acoustic analyzer 102 as described further below) so that top membrane 214 is torn or ruptured, such as at location 222 in FIG. 2C, releasing wash fluid from wash fluid chambers 208a, 208b into glass flow cell 110 through second fluid conduit 120.

In one or more embodiments, a one-way valve 224, such as a check valve, may be provided within first fluid conduit 116 so as to allow sample fluid to travel from sample inlet port 114 to glass flow cell 110, while preventing the flow of wash fluid from wash fluid chambers 208a, 208b toward sample inlet port 114 (e.g., when the glass flow cell 110 is being rinsed with wash fluid).

Figure 3A:
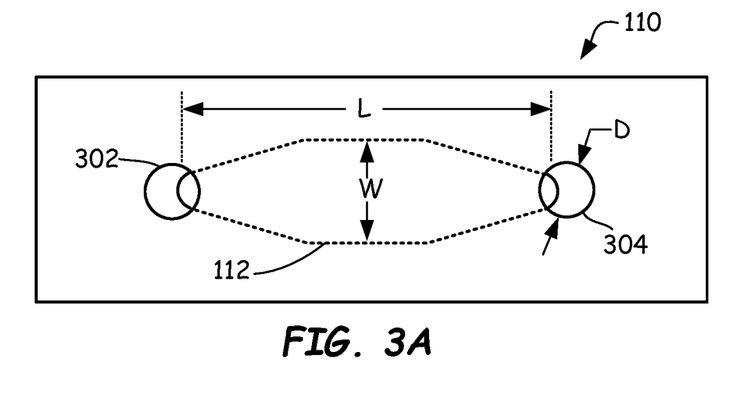
FIG. 3A is a bottom plan view of an example embodiment of a glass flow cell provided herein.
Figure 3B:
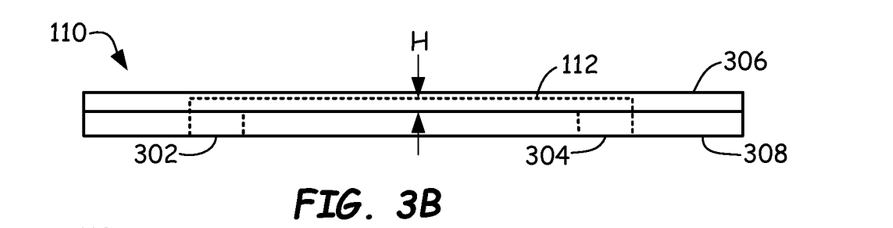
FIG. 3B is a side plan view of an example embodiment of a glass flow cell provided herein.

FIG. 3A is a bottom plan view and FIG. 3B is a side plan view of an example embodiment of glass flow cell 110 provided herein. With reference to FIG. 3A, glass flow cell 110 includes an inlet 302 coupled to a first side of channel 112 and an outlet 304 coupled to a second side of channel 112. In the embodiment of FIGS. 3A and 3B, channel 112 is shown as having an extended, diamond-shape with a length L, a width W (at its widest point), and a height H. Other channel shapes may be used, such as rectangular, cylindrical or the like. In some embodiments, the channel width to height ratio W:H may be about 5:1 or greater, and the channel length L may be about 5 to 10 times the channel width W. Other relationships between channel length, width and/or height may be employed. In some embodiments, channel 112 may have a length L of about 1.25 mm to 20 mm, a width W of about 250 micrometers to 2 mm, and a height H of about 50 to 400 micrometers. Other lengths, heights, and/or widths may be used.

Inlet 302 and/or outlet 304 may comprise a circular or otherwise shaped opening provided a path to channel 112. In some embodiments, inlet 302 and/or outlet 304 may have a diameter of about 100 micrometers to about 2 mm, although other diameters may be used. In general, the inlet 302 and/or outlet 304 may have a diameter that is similar to the width of the channel 112.

Glass flow cell 110 may be formed from any suitable glass such as quartz glass, crown glass, flint glass, another type of optical glass or the like. In some embodiments, a glass with a high acoustic impedance may be employed. Other glass types may be used.

As shown in FIG. 3B, in some embodiments, glass flow cell may be formed from a first glass piece 306 having the channel 112 formed therein and a second glass piece 308 having the inlet 302 and outlet 304 formed therein. (Second glass piece 308 also may serve as a bottom of channel 112.) First glass piece 306 and second glass piece 308 may be coupled together using any suitable mechanism including an adhesive, a mechanical coupling, a combination thereof, or the like. In some embodiments, the first and second glass pieces 306 and 308 may be formed from the same material. Alternatively, different materials (e.g., different types of glass) may be used for the first and second glass pieces 306 and 308.

Figure 3C:
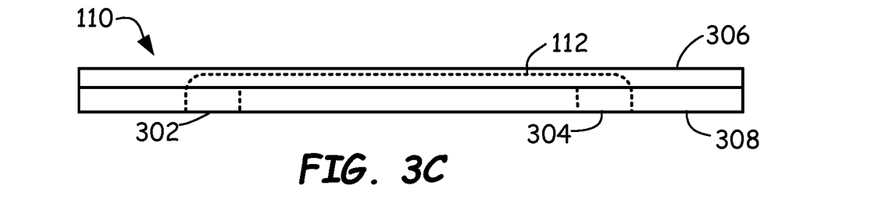
FIG. 3C is a side plan view of an alternative embodiment of a glass flow cell provided herein in which the edges of the channel in the glass flow cell are rounded.

FIG. 3C is a side plan view of an alternative embodiment of glass flow cell 110 provided herein in which the edges of channel 112 are rounded. Other edge shapes may be used.

Figure 3D:
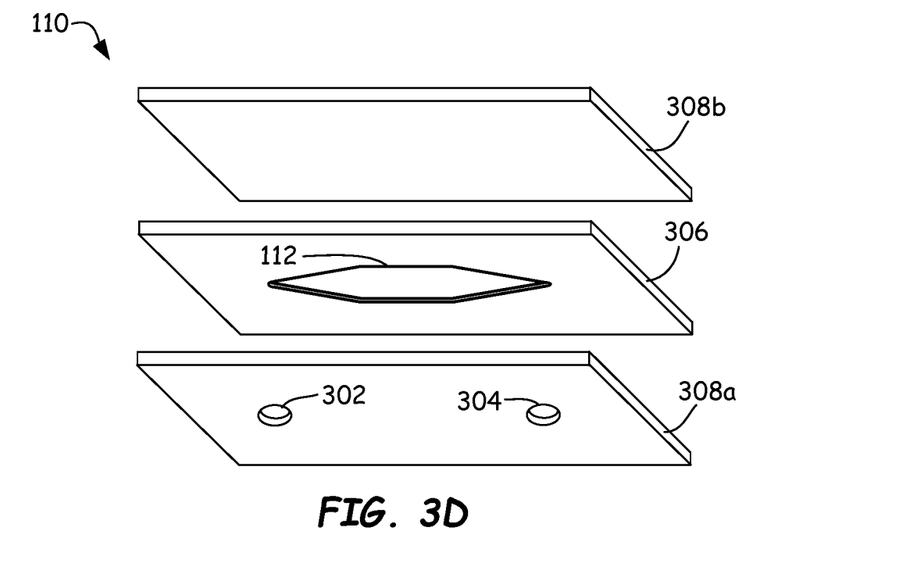
FIG. 3D is an exploded, perspective view of yet another embodiment of a glass flow cell provided herein in which the glass flow cell is formed from three pieces of glass.

FIG. 3D is an exploded, perspective view of yet another embodiment of glass flow cell 110 provided herein in which glass flow cell 110 is formed from three pieces of glass. For example, first glass piece 306 having channel 112 formed therein, a second glass piece 308a having inlet 302 and outlet 304 formed therein, and a third glass piece 308b (e.g., without a channel, an inlet or an outlet) may be coupled together to form glass flow cell 110. Other layouts and/or numbers of glass pieces may be used. The same or different materials may be used for the first, second and third glass pieces 306, 308a and 308b. For example, in some embodiments, a combination of two or more of quartz glass, crown glass, flint glass, and any other optical glass may be used to form a glass flow cell.

Figure 4A:
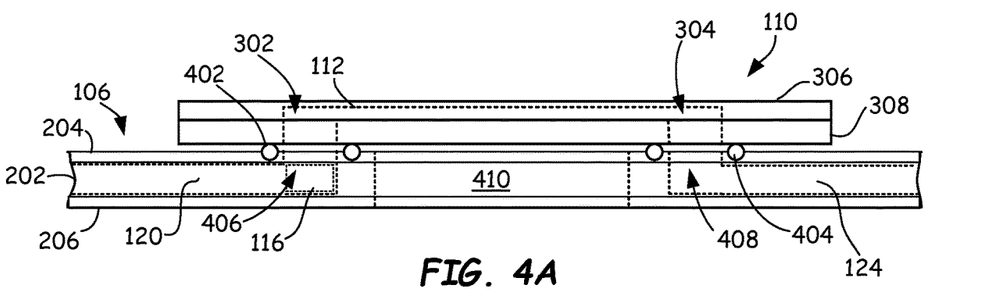
FIG. 4A is a side plan view of an example embodiment of a glass flow cell coupled to a disposable card body in accordance with embodiments provided herein.

FIG. 4A is a side plan view of an example embodiment of glass flow cell 110 coupled to card body 106 provided herein. Only a portion of card body 106 is shown. With reference to FIG. 4A, glass flow cell 110 may be coupled to disposable card body 106 using any suitable mechanism. In some embodiments, a first sealing member 402 may seal inlet 302 of glass flow cell 110 relative to card body 106, and a second sealing member 404 may seal outlet 304 of glass flow cell 110 relative to card body 106. First and second sealing members 402, 404 may be any suitable sealing element including, for example, polyurethane, neoprene, silicone, polytetrafluoroethylene (PTFE) O-rings or other sealing member materials and/or shapes. In some embodiments, first and second sealing members 402 and 404 may be part of card body 106 (e.g., provided within recesses (not shown) formed in card body 106), while in other embodiments, first and second sealing members 402 and 404 may be part of glass flow cell 110.

Disposable card body 106 may include an outlet port 406 that aligns with inlet 302 of glass flow cell 110. Both first fluid conduit 116 (shown as a dashed box in FIG. 3A) and second fluid conduit 120 may couple to outlet port 406. In this manner, sample fluid may be delivered to channel 112 by flowing from sample fluid inlet 114 (FIG. 2A) through first fluid conduit 116 and outlet port 406 of card body 106 into inlet 402 and channel 112 of glass flow cell 110. Likewise, wash fluid may flow from wash fluid region 118 (FIG. 2A) through second fluid conduit 120 and outlet port 406 of card body 106 into inlet 402 and channel 112 of glass flow cell 110.

Disposable card body 106 may also include a waste inlet port 408 that aligns with outlet 304 of gas flow cell 110. Third fluid conduit 124 may couple to waste inlet port 408. In this manner, waste sample fluid and waste wash fluid may be delivered from channel 112 of glass flow cell 110 to waste fluid region 122 of card body 106 by flowing from channel 112 through outlet 304 of glass flow cell 110 into waste inlet port 408 of card body 106 and through third fluid conduit 124 into waste fluid region 122. Through use of outlet port 406 and waste inlet port 408 of card body 106, sample fluid and wash fluid may be supplied from disposable card body 106 to channel 112 of glass flow cell 110, and waste sample fluid and wash fluid may be delivered back to disposable card body 106 so that glass flow cell 110 is available for another measurement on a different sample fluid. After receiving waste sample fluid and waste wash fluid, card body 106 may be discarded.

Figure 4B:
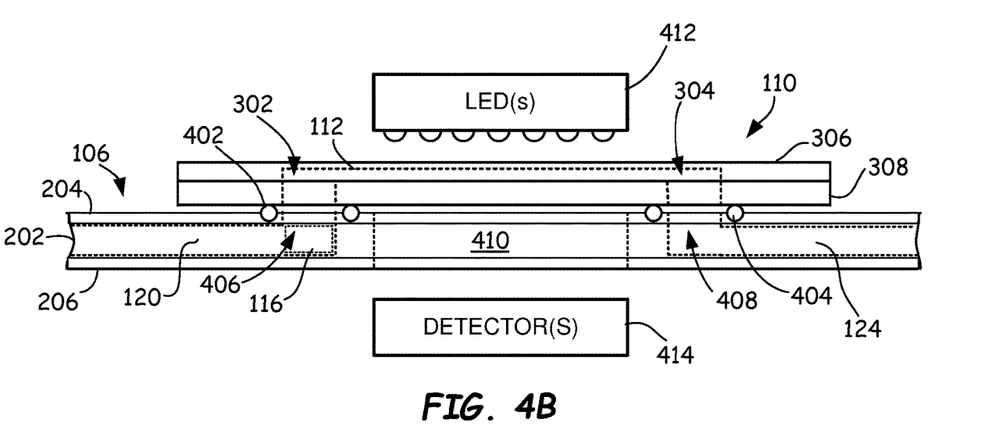
FIG. 4B illustrates one or more LEDs positioned above a channel of a glass flow cell in accordance with embodiments provided herein.

In some embodiments, disposable card body 106 may include an opening 410 (or otherwise optically transparent region) that extends through a width of card body 106 and that aligns with channel 112 of glass flow cell 110. Opening 410 allows optical measurements to be performed on sample fluid contained within channel 112 of glass flow cell 110 as described further below. For example, FIG. 4B illustrates one or more LEDs 412, such an LED string, positioned above channel 112 of glass flow cell 110. A single LED, multiple LEDs (e.g., a linear LED string, a 2-dimensional array of LEDs and/or LED strings, etc.), or any other number or arrangement of one or more LEDs may be used. Other light sources may be used. A detector 414 may be positioned below opening 410 of card body 106 to receive optical signals transmitted from LED(s) 412 after the optical signals travel through channel 112. Information regarding the sample fluid in channel 112 may be obtained by observing what is absorbed by the sample fluid versus what is transmitted through the sample fluid.

LED(s) 412 may include one or more LEDs that emit the same or different wavelengths of light. For example, in some embodiments, LED(s) 412 may contain seven LEDs that emit seven different colors (e.g., red, orange, yellow, green, blue, indigo or violet). Based on the amount and/or color of light transmitted through a sample fluid with channel 112 of glass flow cell 110, acoustic analyzer 102 may probe different characteristics of the sample fluid. For a blood sample, for example, the various color LEDs may probe blood components to detect lipid level, bilirubin level, hemolysis level, free hemoglobin, or the like. Other numbers and/or wavelength-emitting LEDs may be used.

Figure 4C:
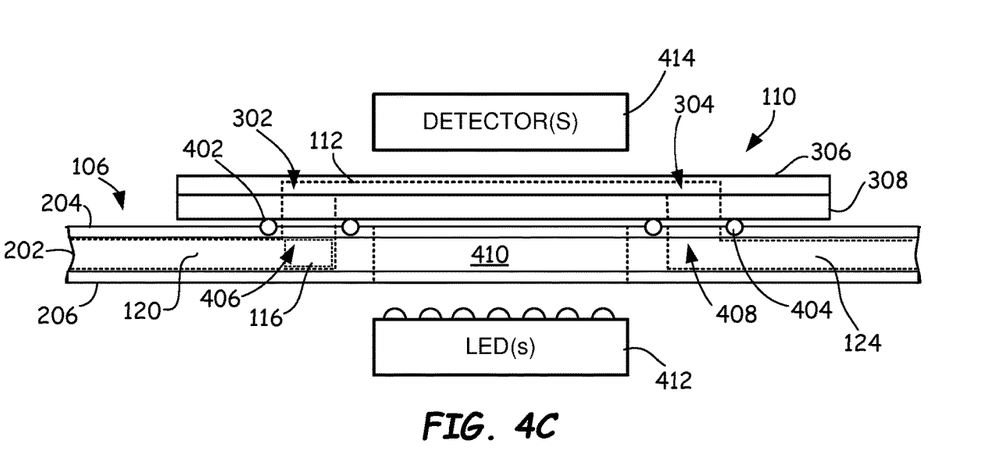
FIG. 4C illustrates an alternative embodiment of one or more LEDs positioned below a channel of a glass flow cell in accordance with embodiments provided herein.

In some embodiments, LED(s) 412 may be located below card body 106 and detector 414 may be located above channel 112 of glass flow cell 110 as shown in FIG. 4C.

Figure 5A:
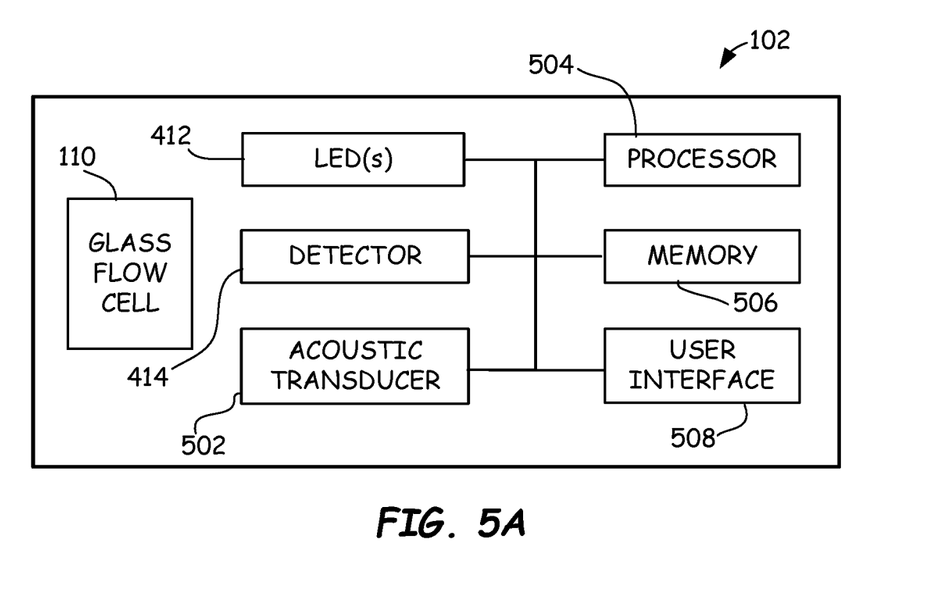
FIG. 5A is a schematic top view of an example embodiment of the acoustic analyzer of FIG. 1A illustrating various components that may be contained within the acoustic analyzer in accordance with embodiments provided herein.

FIG. 5A is a schematic top view of an example embodiment of acoustic analyzer 102 of FIG. 1A illustrating various components that may be contained within acoustic analyzer 102. With reference to FIG. 5A, in some embodiments, acoustic analyzer 102 may include glass flow cell 110, LED(s) 412 and detector 414 as previously described. Additionally, acoustic analyzer 102 may include one or more acoustic transducers, referred to as acoustic transducer 502 in FIG. 5A. More than one acoustic transducer 502 may be used.

Acoustic analyzer 102 may also include a processor 504, a memory 506 and a user interface 508. Processor 504 may be coupled to and/or control operation of LED(s) 412, detector 414, acoustic transducer 502, memory 506 and/or user interface 508.

Acoustic transducer 502 may be an ultrasonic or other frequency transducer configured to generate pressure waves in sample fluid within channel 112 of glass flow cell 110. For example, acoustic transducer 502 may have a frequency selected based on dimensions of channel 112 so that a standing wave pattern is generated within channel 112. The standing wave pattern may cause components of sample fluid within channel 112 to become physically separated. In some embodiments, the standing waves generated by acoustic transducer 502 may cause red blood cells within a blood sample within channel 112 to move away from other components within the blood sample. LED(s) 412 and detector 414 then may be used to probe the remaining blood components to detect concentration level and/or other characteristics of such blood components. Because red blood cells may scatter light, segregating the red blood cells from other blood components may facilitate measurements.

In some embodiments, acoustic transducer 502 may produce pressure waves at a frequency of between about 100 kilohertz to 1 megahertz. Other frequencies may be used.

Processor 504 may be a computational resource such as, but not limited to, a microprocessor, a microcontroller, an embedded microcontroller, a digital signal processor (DSP), a field programmable gate array (FPGA) configured to perform as a microcontroller, or the like.

Memory 506 may be any suitable type of memory, such as, but not limited to, one or more of a volatile memory and/or a non-volatile memory. For example, memory 506 may include a combination of different types of memory such as volatile memory and non-volatile memory. Volatile memory may include, but is not limited to, a static random access memory (SRAM), or a dynamic random access memory (DRAM). Non-volatile memory may include, but is not limited to, an electrically programmable read-only memory (EPROM), an electrically erasable programmable read-only memory (EEPROM), a flash memory, etc. Memory 506 may have a plurality of instructions stored therein that, when executed by processor 504, cause processor 504 to perform various actions specified by one or more of the stored plurality of instructions.

User interface 508 may include one or more of a display screen (e.g., display 108), a touch panel and/or screen, an audio speaker, and a microphone, for example. User interface 508 may be controlled by processor 504, and functionality of user interface 508 may be implemented, at least in part, by computer-executable instructions (e.g., program code or software) stored in memory 506 and/or executed by processor 504 of acoustic analyzer 102. In some embodiments, processor 504 may receive one or more measured results from detector 414, process the measured results to generate calculated results, and present the calculated results and/or other information, such as patient information, via user interface 508. For example, user interface 508 may be configured to present one or more measured and/or calculated results to a user of acoustic analyzer 102.

Figure 5B:
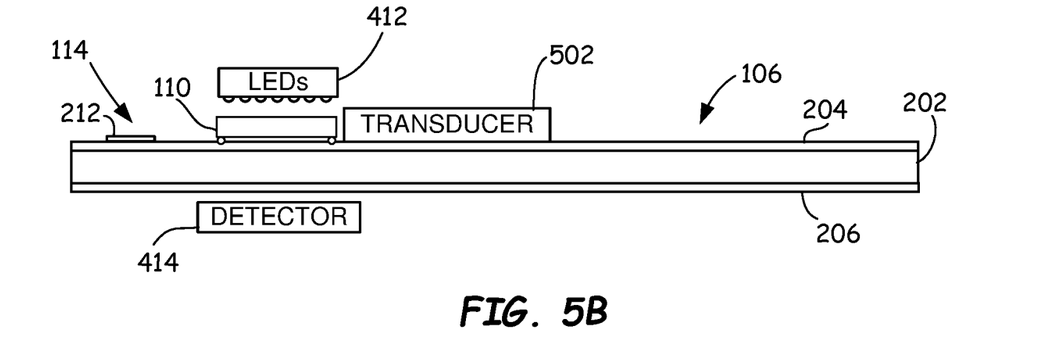
FIG. 5B is a side plan view illustrating an example layout of a glass flow cell, one or more LEDs, a detector and an acoustic transducer when a disposable card body is inserted into the acoustic analyzer of FIG. 5A.

FIG. 5B is a side plan view illustrating an example layout of glass flow cell 110, one or more LED(s) 412, detector 414 and acoustic transducer 502 when card body 106 is inserted into acoustic analyzer 102. Other locations may be used for glass flow cell 110, LED(s) 412, detector 414 and/or acoustic transducer 502.

Figure 5C:
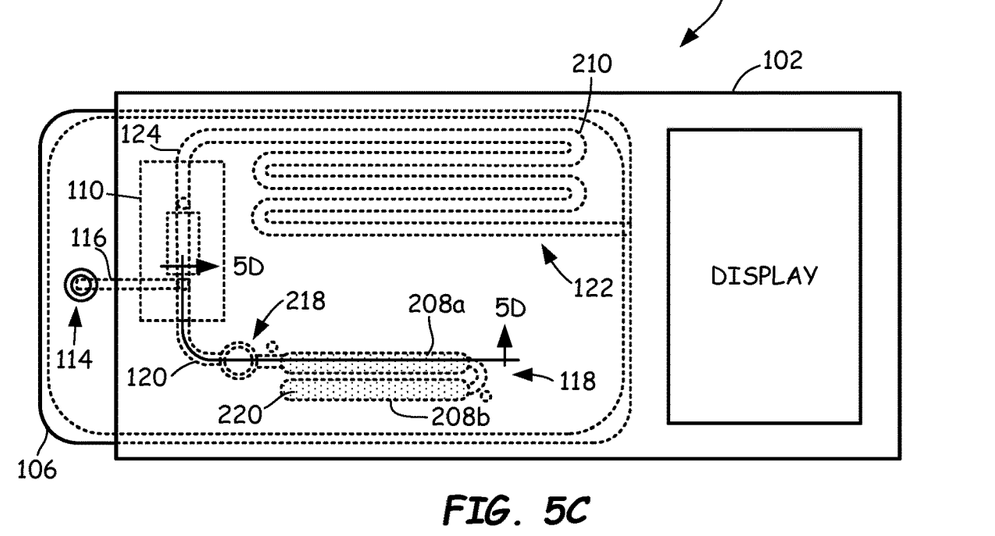
FIG. 5C is a top plan view of an example embodiment of the acoustic analyzer system of FIG. 5B provided herein.

FIG. 5C is a top plan view of an example embodiment of acoustic analyzer system 100 provided herein. As shown in FIG. 5C, disposable card body 106 is inserted into acoustic analyzer 102 so that it interfaces with glass flow cell 110. For example, glass flow cell 110 may be positioned within acoustic analyzer 102 such that the inlet 302 and outlet 304 of glass flow cell 110 align with the outlet port 406 and waste inlet port 408, respectively, of disposable card body 106 after card body 106 is fully inserted into opening 104 (FIG. 1B) of acoustic sensor 102. A pressure sensitive switch (not shown) or other mechanism may detect the presence of card body 106 when it is fully inserted, and user interface 508 may indicate to a user whether card body 106 is properly positioned within acoustic analyzer 102 (and/or prevent analysis by acoustic analyzer 102 if card body 106 is not fully inserted).

Once card body 106 is properly positioned with acoustic analyzer 102, acoustic analyzer 102 may press card body 106 against glass flow cell 110, or glass flow cell 110 may be pressed against card body 106, so that sealing members 402 and 404 seal inlet 302 and outlet 304 of glass flow cell 110 relative to outlet port 406 and waste inlet port 408, respectively, of disposable card body 106. For example, opening 104 of acoustic analyzer 102 may be sized so that card body 106 is pressed against glass flow cell 110 upon insertion within acoustic analyzer 102. Alternatively, a support member (not shown) within opening 104 may apply pressure against card body 106 upon insertion that biases card body 106 against glass flow cell 110. In yet another embodiment, glass flow cell 110 may be lowered into contact with card body 106 after card body 106 is inserted into opening 104 of acoustic analyzer 102. Other mechanisms for sealing card body 106 relative to glass flow cell 110 may be employed.

With reference to FIG. 5C, sample inlet port 114 of card body 106 is positioned to receive sample fluid, such as a blood sample contained within a syringe, and to employ first fluid conduit 116 of disposable card body 106 to deliver the sample fluid to channel 112 of glass flow cell 110. Acoustic analyzer 102 may then perform one or more measurements on the sample fluid (e.g., acoustophoresis-assisted hemolysis analysis or another measurement) within channel 112 of glass flow cell 110 using transducer 502 (FIGS. 5A and 5B) to position one or more sample components, and LED(s) 412 and detector 414 to perform measurements on one or more components of the sample fluid. In some embodiments in which the sample fluid is a blood sample, one or more wavelengths of light (e.g., red, orange, yellow, green, blue, indigo or violet) may be used to probe the blood components to detect lipid level, bilirubin level, hemolysis level, free hemoglobin, or the like. Such information may be collected by processor 504 and/or displayed on user interface 508 (or otherwise communicated to a user of acoustic analyzer system 100).

Figure 5D:
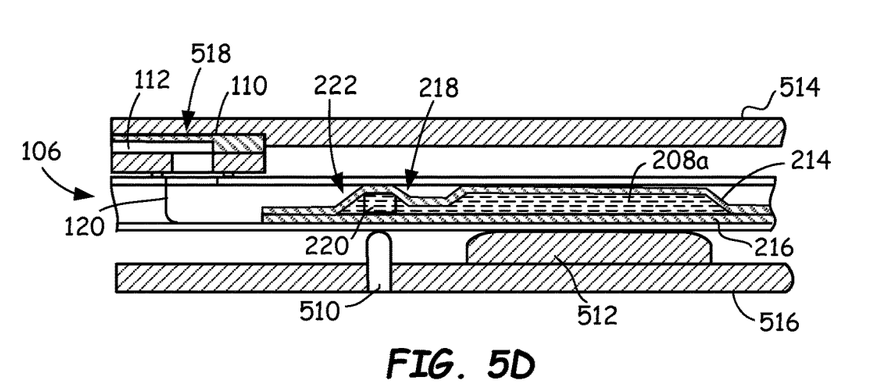
FIG. 5D illustrates an example cross section view of the disposable card body taken along fluidic path 5D-5D in FIG. 5C in accordance with one or more embodiments provided herein.

Following measurements within glass flow cell 110, wash fluid may be provided to channel 112 from wash fluid chambers 208a and/or 208b through second fluid conduit 120. In some embodiments, valve 218 may limit wash fluid flow within second fluid conduit 120 and glass flow cell 110. For example, FIG. 5D illustrates an example cross section view of disposable card body 106 taken along fluidic path 5D-5D in FIG. 5C in accordance with one or more embodiments provided herein. As shown in FIG. 5D, movable plug 220 may block flow of wash fluid from wash fluid chamber 208a (and/or wash fluid chamber 208b) into second fluid conduit 120 and glass flow cell 110. To initiate washing of glass flow cell 110, movable plug 220 may be elevated by a pin element 510 within acoustic analyzer 102 so that top membrane 214 is torn or ruptured, such as at location 222 in FIG. 5D, releasing wash fluid from wash fluid chambers 208a, 208b into glass flow cell 110 through second fluid conduit 120 (as shown in the cross-section view of FIG. 5E). Similarly, and in some case simultaneously therein, acoustic analyzer 102 may employ an actuator element 512 that compresses wash fluid chamber 208a and/or wash fluid chamber 208b so as to push wash fluid into second fluid conduit 120, through channel 112 of glass flow cell 110 and into waste fluid region 122 (serpentine fluid conduit 210 in FIG. 5C). In this manner, waste sample fluid and waste wash fluid travel through third fluid conduit 124 for storage in waste fluid region 122 of disposable card body 106. Disposable card body 106 may then be removed from acoustic analyzer 102 and discarded, leaving glass flow cell 110 ready to receive another sample delivered using a different disposable card body (not shown).

Figure 5E:
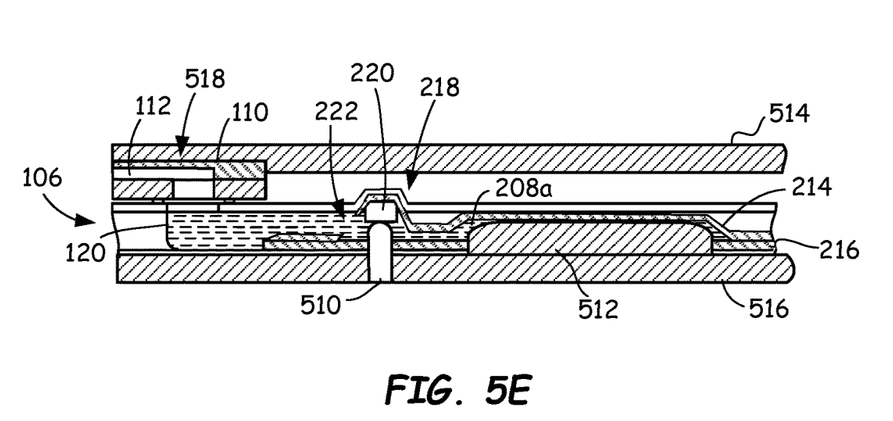
FIG. 5E illustrates an example cross section view of the disposable card body taken along fluidic path 5D-5D in FIG. 5C illustrating the opening of a valve in accordance with one or more embodiments provided herein.

As shown in FIGS. 5D and 5E, in some embodiments, glass flow cell 110 may be coupled to an upper support member 514 and pin element 510 and/or actuator element 512 may be coupled to a (moveable) lower support element 516 of acoustic analyzer 102. Other methods of supporting and/or moving glass flow cell 110, pin element 510 and/or actuator element 512 may be used. In the embodiment of FIGS. 5D and 5E, a mounting location 518, such as a notched region, is provided within upper support member 514 for supporting glass flow cell 110 (e.g., via an adhesive, screw, bolt or other securing mechanism). Other mounting locations and/or methods may be used.

In some embodiments, the wash fluid may be a bleach or other wash fluid solution. For example, a 5% to 20% bleach solution may be used for the wash fluid stored on disposable card body 106. Other bleach solution concentrations and/or wash fluids may be used.

Figure 6:
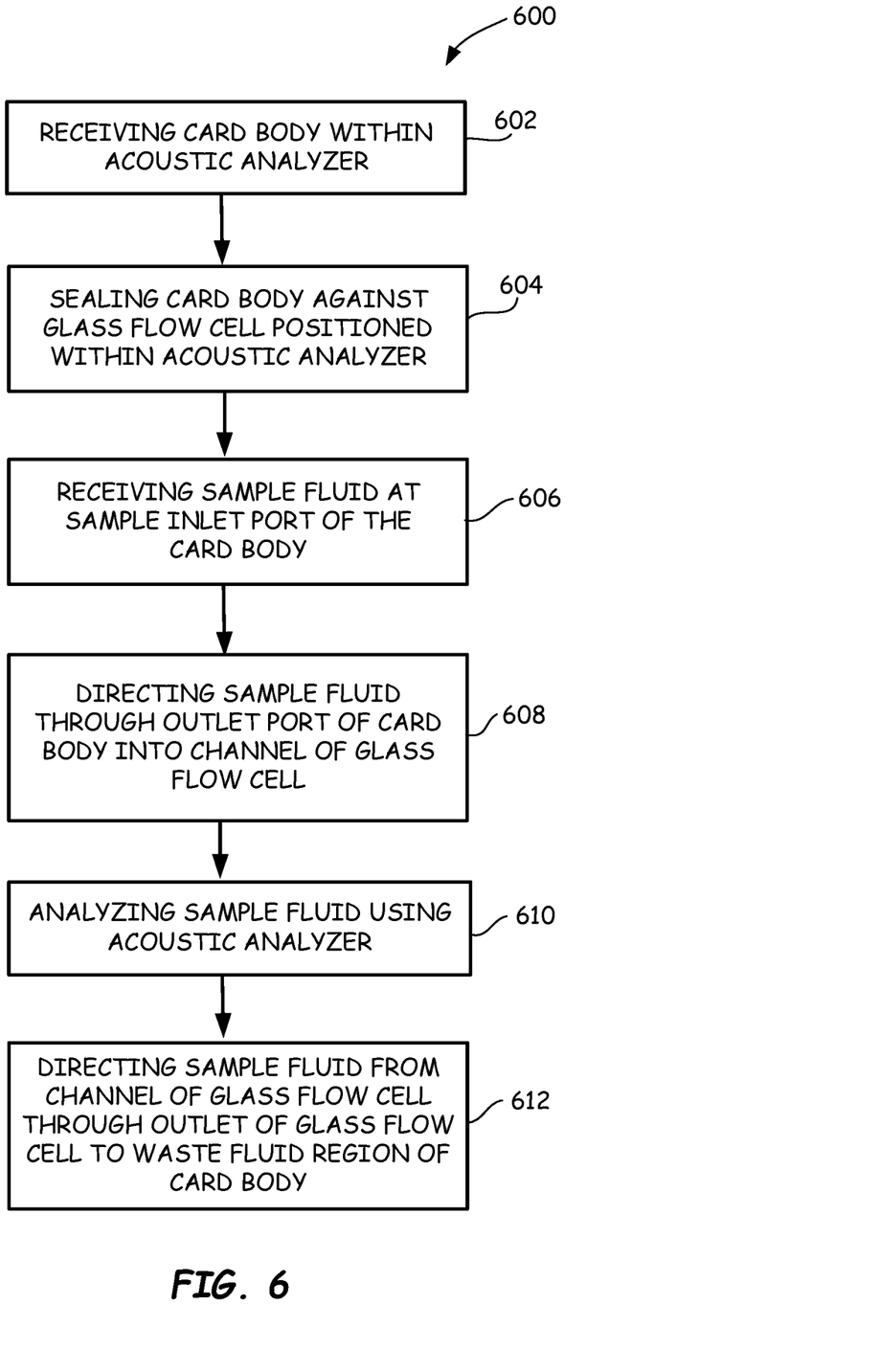
FIG. 6 is a flowchart of an example method of using the acoustic analyzer system of FIG. 1A in accordance with embodiments of the present disclosure.

FIG. 6 is a flowchart of an example method 600 of using acoustic analyzer system 100 in accordance with embodiments of the present disclosure. Method 600 begins with Block 602 at which a disposable card body is received within the acoustic analyzer. For example, disposable card body 106 may be inserted into opening 104 in acoustic analyzer 102. In some embodiments, prior to use of acoustic analyzer 102, display 108 and/or user interface 508 may prompt a user to enter user identification, scan a name tag or other barcode, enter a password or otherwise authenticate their identity.

Once the card body has been inserted into the acoustic analyzer, in Block 604, the card body is sealed against the glass flow cell positioned within the analyzer. For example, sealing member 402 and 404 may seal glass flow cell 110 relative to card body 106.

In Block 606, a sample fluid is received at the sample inlet port of the disposable card body. The sample fluid then may be directed through the outlet port of the disposable card body into the channel of the glass flow cell (in Block 608). For example, a syringe or other sample fluid storage and/or delivery device may be employed to interface with sample inlet port 114 of card body 106. The syringe or other device may move sample fluid through sample inlet port 114, through first fluid conduit 116, through outlet 406 of card body 106, through inlet 302 of glass flow cell 110 and into channel 112.

Once sample fluid is located within the channel of the glass flow cell, in Block 610, the acoustic analyzer may analyze the sample fluid. For example, acoustic analyzer 102 may perform one or more measurements on the sample fluid within channel 112 of glass flow cell 110 using transducer 502 (FIGS. 5A and 5B) to position one or more sample fluid components, and LED(s) 412 and detector 414 to perform measurements on one or more sample fluid components. In some embodiments in which the sample fluid is a blood sample, ultrasonic energy from transducer 502 may be used to separate red blood cells from plasma within channel 112 and/or one or more wavelengths of light from LED(s) 412 may be used to probe blood components to detect lipid level, bilirubin level, hemolysis level, free hemoglobin, or other blood component characteristics. Such information may be collected by processor 504 and/or displayed on user interface 508 (or otherwise communicated to a user of acoustic analyzer system 100).

In some embodiments, measurements may be performed on sample fluid while it is stationary within channel 112 of glass flow cell 110. In other embodiments, measurements may be performed while sample fluid travels through channel 112. Sample fluid amounts of less than 10 microliters may be employed in some embodiments, although other sample fluid amounts may be used.

Following measurements by the acoustic analyzer, in Block 612, the sample fluid within the channel of the glass flow cell may be directed through the outlet of the glass flow cell to the waste fluid region of the disposable card body. For example, wash fluid from wash fluid region 118 may be directed into second fluid conduit 120 of card body 106, through outlet port 406, through channel 112 of glass flow cell 110, through waste inlet port 408 of card body 106, and into waste fluid region 122 (serpentine fluid conduit 210 in FIG. 5A). In this manner, waste sample fluid and waste wash fluid travel through third fluid conduit 124 for storage in waste fluid region 122 of disposable card body 106. Disposable card body 106 may then be removed from acoustic analyzer 102 and discarded, leaving glass flow cell 110 ready to receive another sample delivered using a different disposable card body.

By interfacing the disposable card body with the glass flow cell within the analyzer, components of a sample fluid may be manipulated within the glass flow cell using acoustic techniques, and the disposable card body may be used for sample fluid and wash fluid delivery, as well as for waste fluid disposal. In some embodiments, the glass flow cell may be re-used within acoustic analyzer 102 between 100 to 1000 times before replacement.

Disposable card body 106 and glass flow cell 110 may be part of and/or form a "diagnostic card assembly" that may be used in an acoustic analyzer for performing acoustic-wave assisted measurements, such as acoustophoresis-assisted hemolysis analysis.

The foregoing description discloses only example embodiments of the invention; modifications of the above disclosed apparatus and methods which fall within the scope of the invention will be readily apparent to those of ordinary skill in the art. Accordingly, while the present invention has been disclosed in connection with the example embodiments thereof, it should be understood that other embodiments may fall within the spirit and scope of the invention, as defined by the following claims.

ILLUSTRATIVE EMBODIMENTS

1. A diagnostic card assembly for use in an acoustic analyzer, comprising:
a card body configured for insertion into an acoustic analyzer, the card body including:
a sample inlet port positioned to receive sample fluid;
a waste inlet port;
an outlet port;
a first fluid conduit extending between the sample inlet port and the outlet port;
a wash fluid chamber configured to hold a wash fluid;
a second fluid conduit extending between the wash fluid chamber and the outlet port;
a valve connecting the wash fluid chamber to the second fluid conduit and configured to control flow of wash fluid from the wash fluid chamber when the card body is inserted into the acoustic analyzer;
a waste fluid region configured to store waste sample fluid and waste wash fluid; and
a third fluid conduit extending between the waste input port and the waste fluid region;
wherein the card body is configured to be inserted into an acoustic analyzer and to sealingly couple to a glass flow cell within the acoustic analyzer, deliver sample fluid and wash fluid through the outlet port of the card body to a channel of the glass flow cell, and receive waste sample fluid and waste wash fluid from the glass flow cell.

2. The diagnostic card assembly of claim 1, wherein the card body is formed from polycarbonate plastic.

3. The diagnostic card assembly of claim 1, wherein the waste fluid region includes a serpentine fluid conduit.

4. An acoustic analyzer comprising:
an opening configured to receive a disposable card body having a sample inlet port, a waste inlet port, an outlet port, a wash fluid chamber and a waste fluid region;
a mounting location positioned within the opening and configured to hold a replaceable, multi-use glass flow cell within the acoustic analyzer such that the glass flow cell sealingly couples to the disposable card body when the disposable card body is inserted into the acoustic analyzer; and
a transducer configured to generate standing waves in a channel of any glass flow cell positioned within the mounting location so as to spatially separate one or more components of a sample fluid within the channel.

5. The acoustic analyzer of claim 4, further comprising: a light source configured to illuminate a sample fluid within a channel of any glass flow cell positioned within the mounting location; and
a detector configured to detect light from the light source after the light travels through the sample fluid.

6. The acoustic analyzer of claim 5, wherein the acoustic analyzer is configured to employ the transducer to separate red blood cells from other components of a blood sample within a channel of a glass flow cell mounted at the mounting location of the acoustic analyzer.

7. The acoustic analyzer of claim 6, wherein the acoustic analyzer is configured to employ the light source and detector to detect one or more of lipid level, bilirubin level, hemolysis level and free hemoglobin.

8. The acoustic analyzer of claim 1, wherein the acoustic analyzer is configured to compress a portion of a disposable card body positioned within the opening of the acoustic analyzer so as to direct wash fluid from the disposable card body through a channel of a glass flow cell mounted at the mounting location of the acoustic analyzer.

9. An acoustic analyzer system comprising:
an acoustic analyzer configured to receive a disposable card body; and
a replaceable, multi-use glass flow cell positioned within the acoustic analyzer and configured to sealingly couple to the disposable card body when the disposable card body is inserted into the acoustic analyzer, the glass flow cell including:
an inlet, an outlet and a channel extending between the inlet and the outlet;
wherein the inlet of the glass flow cell is configured to receive sample fluid and wash fluid from an outlet port of the disposable card body, direct flow of sample fluid and wash fluid through the channel and to the outlet of the glass flow cell; and
wherein the outlet of the glass flow cell is configured to provide sample fluid and wash fluid to a waste inlet port of the disposable card body.

10. The acoustic analyzer system of claim 9, wherein the acoustic analyzer is configured to employ acoustophoresis on sample fluid within the channel of the replaceable, multi-use glass flow cell.

11. The acoustic analyzer system of claim 9, wherein the first glass piece and the second glass piece are made of a same material.

12. The acoustic analyzer system of claim 9, wherein the glass flow cell is a multi-use glass flow cell.

What is claimed is:
1. A diagnostic card assembly for use in an acoustic analyzer, comprising:
a card body configured for insertion into an acoustic analyzer, the card body including:
a sample inlet port positioned to receive sample fluid;
a waste inlet port;
an outlet port;
a first fluid conduit extending between the sample inlet port and the outlet port;
a wash fluid chamber configured to hold a wash fluid;
a second fluid conduit extending between the wash fluid chamber and the outlet port;
a valve connecting the wash fluid chamber to the second fluid conduit and configured to control flow of wash fluid from the wash fluid chamber when the card body is inserted into the acoustic analyzer;
a waste fluid region configured to store waste sample fluid and waste wash fluid; and
a third fluid conduit extending between the waste input port and the waste fluid region;
wherein the card body is configured to be inserted into an acoustic analyzer and to sealingly couple to a glass flow cell within the acoustic analyzer, deliver sample fluid and wash fluid through the outlet port of the card body to a channel of the glass flow cell, and receive waste sample fluid and waste wash fluid from the glass flow cell.

2. The diagnostic card assembly of claim 1, wherein the card body is a disposable, single-use card body.

3. The diagnostic card assembly of claim 1, wherein the card body includes a sealing member configured to seal the card body against the glass flow cell.

4. The diagnostic card assembly of claim 1, wherein the card body includes a one-way valve within the first fluid conduit that prevents wash fluid from the wash fluid chamber from flowing toward the sample inlet port.

5. An acoustic analyzer system comprising:
an acoustic analyzer configured to receive a disposable card body; and
a replaceable, multi-use glass flow cell positioned within the acoustic analyzer and configured to sealingly couple to the disposable card body when the disposable card body is inserted into the acoustic analyzer, the glass flow cell including:
an inlet, an outlet and a channel extending between the inlet and the outlet;
wherein the inlet of the glass flow cell is configured to receive sample fluid and wash fluid from an outlet port of the disposable card body, direct flow of sample fluid and wash fluid through the channel and to the outlet of the glass flow cell; and
wherein the outlet of the glass flow cell is configured to provide sample fluid and wash fluid to a waste inlet port of the disposable card body.

6. The acoustic analyzer system of claim 5, wherein the acoustic analyzer is configured to open a valve on the disposable card body that connects a wash fluid chamber of the disposable card body to the outlet port of the disposable card body.

7. The acoustic analyzer system of claim 6, wherein the acoustic analyzer is configured to compress the wash fluid chamber of the disposable card body so has to move wash fluid into the channel of the glass flow cell, thereby washing the glass flow cell.

8. The acoustic analyzer system of claim 5, wherein the acoustic analyzer includes a transducer configured to produce a standing wave within the channel of the glass flow cell.

9. The acoustic analyzer system of claim 5, wherein the glass flow cell is formed from optical glass.

10. The acoustic analyzer system of claim 5, wherein the channel of the glass flow cell has a channel width to channel height ratio of 5:1 or greater and a channel length of 5 to 10 times the channel width.

11. The acoustic analyzer system of claim 5, wherein the glass flow cell includes a first glass piece having the channel formed therein and a second glass piece coupled to the first glass piece and having the inlet and the outlet formed therein.

12. The acoustic analyzer system of claim 5, wherein the glass flow cell is configured to be used between 100 and 1000 times before being replaced.

13. A method of using an acoustic analyzer comprising:
receiving a card body within the acoustic analyzer, the card body including:
- a sample inlet port positioned to receive sample fluid;
- a waste inlet port;
- an outlet port;
- a first fluid conduit extending between the sample inlet port and the outlet port;
- a wash fluid chamber configured to hold a wash fluid;
- a second fluid conduit extending between the wash fluid chamber and the outlet port;
- a valve connecting the wash fluid chamber to the second fluid conduit and configured to control flow of wash fluid from the wash fluid chamber when the card body is inserted into the acoustic analyzer;
- a waste fluid region configured to store waste sample fluid and waste wash fluid; and
- a third fluid conduit extending between the waste inlet port and the waste fluid region;

sealing the card body against a glass flow cell positioned with the acoustic analyzer, the glass flow cell including:
- an inlet, an outlet and a channel extending between the inlet and the outlet;
- wherein the inlet of the glass flow cell is configured to receive sample fluid and wash fluid from the outlet port of the card body, direct flow of sample fluid and wash fluid through the channel and to the outlet of the glass flow cell; and
- wherein the outlet of the glass flow cell is configured to provide sample fluid and wash fluid to the waste inlet port of the card body;

receiving a sample fluid at the sample inlet port of the card body;

directing the sample fluid through the first fluid conduit, through the outlet port of the card body and through the inlet of the glass flow cell into the channel of the glass flow cell;

analyzing the sample fluid using the acoustic analyzer; and directing the sample fluid from the channel of the glass flow cell through the outlet of the glass flow cell, through the waste inlet port of the card body, and through the third fluid conduit to the waste fluid region of the card body.

14. The method of claim 13 wherein directing sample fluid through the first fluid conduit comprises employing a syringe to direct sample fluid through the first fluid conduit.

15. The method of claim 13 further comprising directing wash fluid from the wash fluid chamber of the card body through the second fluid conduit, through the outlet port of the card body, through the inlet of the glass flow cell, through the channel of the glass flow cell, through the outlet of the glass flow cell, through the waste inlet port of the card body, and through the third fluid conduit to the waste fluid region of the card body.

16. The method of claim 15 wherein directing wash fluid comprises employing the acoustic analyzer to compress the wash fluid chamber.

17. The method of claim 14 further comprising employing the acoustic analyzer to rupture a membrane to supply wash fluid to the channel of the glass flow cell.

18. The method of claim 14 further comprising, employing wash fluid to clean the glass flow cell after each use.

19. The method of claim 14 further comprising, disposing of the card body after use.

20. The method of claim 14 further comprising, replacing the glass flow cell after 100 to 1000 uses.

* * * * *